(12) United States Patent
Berg

(10) Patent No.: US 11,986,601 B2
(45) Date of Patent: May 21, 2024

(54) HARMONIZATION DEVICES AND METHODS

(71) Applicant: Sigmar Paul Berg, Malibu, CA (US)

(72) Inventor: Sigmar Paul Berg, Malibu, CA (US)

(73) Assignee: Sigmar Paul Berg, Malibu, CA (US)

( * ) Notice: Subject to any disclaimer, the term of this patent is extended or adjusted under 35 U.S.C. 154(b) by 0 days.

(21) Appl. No.: 18/319,488

(22) Filed: May 18, 2023

(65) Prior Publication Data
US 2023/0285713 A1 Sep. 14, 2023

Related U.S. Application Data

(63) Continuation of application No. 16/765,223, filed as application No. PCT/US2019/052871 on Sep. 25, 2019.

(60) Provisional application No. 62/740,805, filed on Oct. 3, 2018.

(51) Int. Cl.
*A61M 21/02* (2006.01)
*A61M 21/00* (2006.01)
*G10K 5/00* (2006.01)

(52) U.S. Cl.
CPC ............... *A61M 21/02* (2013.01); *G10K 5/00* (2013.01); *A61M 2021/0027* (2013.01); *A61M 2205/076* (2013.01); *A61M 2209/088* (2013.01)

(58) Field of Classification Search
CPC .......... A61M 21/00; A61M 2021/0027; A61M 2205/076; A61M 2209/088; A61M 21/02; G10K 5/00; G10D 7/06

USPC ..................................................... 600/26–28
See application file for complete search history.

(56) References Cited

U.S. PATENT DOCUMENTS

| | | | | |
|---|---|---|---|---|
| 4,054,134 A * | 10/1977 | Kritzer | ............. | A63B 21/00069 482/13 |
| 4,915,660 A * | 4/1990 | Overholt, Sr. | ...... | A01M 31/004 446/209 |
| 5,027,685 A * | 7/1991 | Lenz | ........................ | G10D 9/08 84/385 P |
| 5,803,785 A * | 9/1998 | Primos, Jr. | .......... | A01M 31/004 446/188 |
| 6,231,418 B1 * | 5/2001 | Hancock | ............. | A01M 31/004 446/397 |
| 6,702,769 B1 * | 3/2004 | Fowler-Hawkins | .. | A61M 16/08 482/13 |
| 2003/0060121 A1 * | 3/2003 | Oathout | ................ | B63B 25/002 446/208 |
| 2008/0009222 A1 * | 1/2008 | Lombardi | ........... | A01M 31/004 446/207 |
| 2009/0272311 A1 * | 11/2009 | Shishido | .................. | G10K 5/00 116/137 R |
| 2012/0067191 A1 * | 3/2012 | Heiter-Kelly | ............ | G10G 1/00 84/312 R |
| 2013/0178695 A1 * | 7/2013 | Heiter-Kelly | ............ | G10G 1/00 600/28 |

(Continued)

OTHER PUBLICATIONS

Frequencies of Musical Notes, Simon Paul, 2010 (see attached) (Year: 2010).*

(Continued)

*Primary Examiner* — Sunita Reddy
(74) *Attorney, Agent, or Firm* — ORBIT IP, LLP

(57) ABSTRACT

Devices and methods are described that aid in harmonizing a person with their bodies and/or their environment.

15 Claims, 2 Drawing Sheets

(56) References Cited

U.S. PATENT DOCUMENTS

| | | | |
|---|---|---|---|
| 2015/0243265 A1* | 8/2015 | Laukat | G10D 7/00 |
| | | | 84/398 |
| 2015/0360079 A1* | 12/2015 | Keller | A61M 16/0006 |
| | | | 482/13 |
| 2017/0189749 A1* | 7/2017 | Keller | A63B 21/0004 |
| 2021/0178094 A1* | 6/2021 | Soma | A61M 16/0006 |

OTHER PUBLICATIONS

Mathematical Harmonies, Mark Petersen, Jul. 2001 (see attached) (Year: 2001).*
Baron & Baron Inc, Baron-Jewelry-ballpoint 'Stylus' pen necklace, May 19, 2017 (3 pages, see attached) (Year: 2017).*

* cited by examiner

HARMONIZATION DEVICES AND METHODS

CROSS-REFERENCE TO RELATED APPLICATIONS

This application is a continuation of U.S. application Ser. No. 16/765,223, filed on May 19, 2020, a National Stage Entry of International Application No. PCT/US19/52871, filed on Sep. 25, 2019, which claims the benefit of U.S. Provisional Application No. 62/740,805, filed on Oct. 3, 2018, the contents all of which are herein incorporated by reference in their entireties.

BACKGROUND

Field

Aspects of the present disclosure generally relate to meditative and self-healing devices and methods, and more specifically to harmonization devices and methods.

Background

The advances made by modern society that make human existence easier, e.g., mass transit, telecommunications, large scale production of food and clothing, etc., have also brought increased stress, new viruses and other attacks on human immune systems, and other factors that reduce the quality of human life.

Ancient practices, such as meditation and chanting, have been thought to reduce the deleterious effects of modern life. However, many people find it difficult to practice these techniques with any success for various reasons, e.g., environmental conditions, emotional imbalance, and/or training requirements to practice various techniques are not well understood or interfere with the ability to achieve meaningful results.

SUMMARY

In an aspect of the present disclosure, devices and methods are described that aid in harmonizing a person with their bodies and/or their environment.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further purposes and advantages, will be better understood from the following description when considered in connection with the accompanying figures. It is to be expressly understood, however, that each of the figures is provided for the purposes of illustration and description only and is not intended as a definition of the limits of the present disclosure.

BRIEF DESCRIPTION OF THE DRAWINGS

For a more complete understanding of the present disclosure, reference is now made to the following description taken in conjunction with the accompanying drawings.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent to those skilled in the art, however, that these concepts may be practiced without these specific details. In some instances, well-known structures and components are shown in block diagram form in order to avoid obscuring such concepts. As described herein, the use of the term "and/or" is intended to represent an "inclusive OR", and the use of the term "or" is intended to represent an "exclusive OR".

Overview

Figure 1:
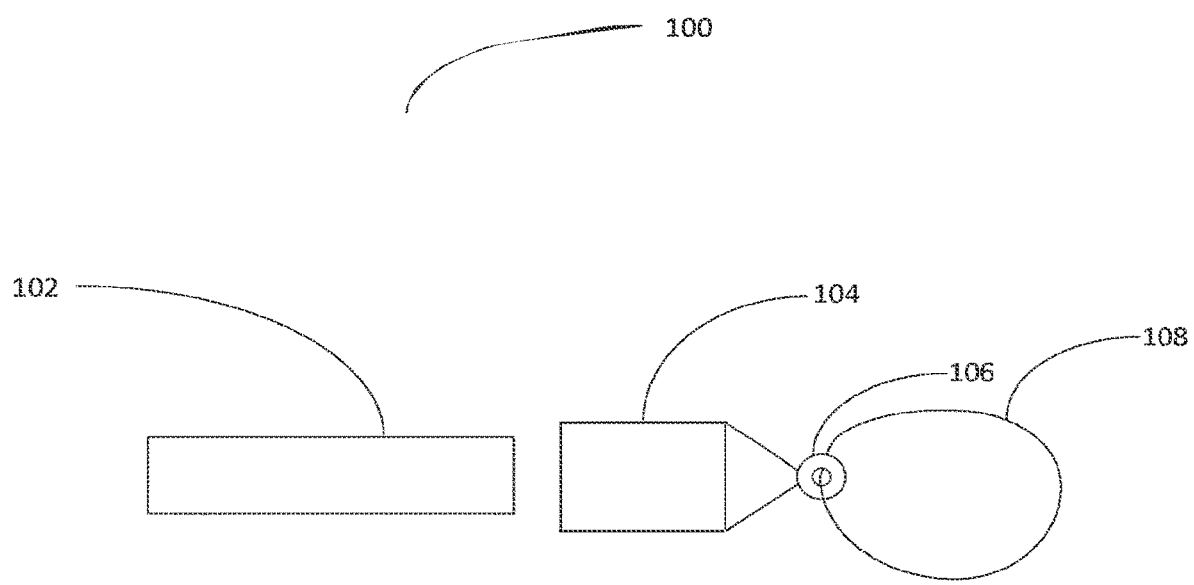
FIG. 1 illustrates a device in accordance with an aspect of the present disclosure.

FIG. 1 illustrates a device in accordance with an aspect of the present disclosure.

As shown in FIG. 1, device 100 comprises a cylinder 102 (also referred to as a "body" herein) and a cap 104. Cap 104 may have an optional ring 106, which may be used with optional chain 108.

Cylinder 102 may be made from steel, brass, copper, aluminum, wood, tin, ceramics, other materials, etc., and/or a combination of materials without departing from the scope of the present disclosure. Cylinder 102 may also be coated with another material, e.g., chrome, aluminum, ceramic, and/or combination of materials without departing from the scope of the present disclosure. Cylinder 102 may be of any length, but often is of a length that is easily carried and/or worn by a person. Cylinder 102 may also take other shapes, e.g., square, hexagonal, conical, etc., without departing from the scope of the present disclosure.

Cap 104 may be made from steel, brass, copper, aluminum, wood, tin, ceramics, other materials, etc., and/or a combination of materials without departing from the scope of the present disclosure. Cap 104 may also be coated with another material, e.g., chrome, aluminum, ceramic, and/or combination of materials without departing from the scope of the present disclosure. Cap 104 is shown as being a bell shaped object, but cap 104 may also take other shapes, e.g., square, hexagonal, conical, etc., without departing from the scope of the present disclosure. In other words, cylinder 102 and/or cap 104 may, either or both, comprise a cross section that may be circular, oval, square, hexagonal, etc., and such cross-sections may not be the same for a given device 100. Cap 104 contacts cylinder 102, and may cover at least one end of cylinder 102.

Optional ring 106 and optional chain 108 may be used with device 100 to provide ease of carrying device 100. For example, and not by way of limitation, optional ring 106 to place device 100 on a necklace-length chain 108 such that device 100 is available to a user at various times during any given day. Chain 108 may be a chain, such as a steel-ball chain, nickel plated chain, stainless steel chain, silver chain, gold chain, copper chain, brass chain, leather cord, waxed cotton cord, hemp string, wooden ball chain, gem stone chain comprising additional devices such as crystals, quartz, gems, etc., a mala bead chain, a glass ball chain, and/or other types of devices for holding device 100. Chain 108 may also be made of one or more materials, and/or may also be a cord, rope, and/or other length of material without departing from the scope of the present disclosure. Further, chain 108 may be of any length as desired.

Figure 2:
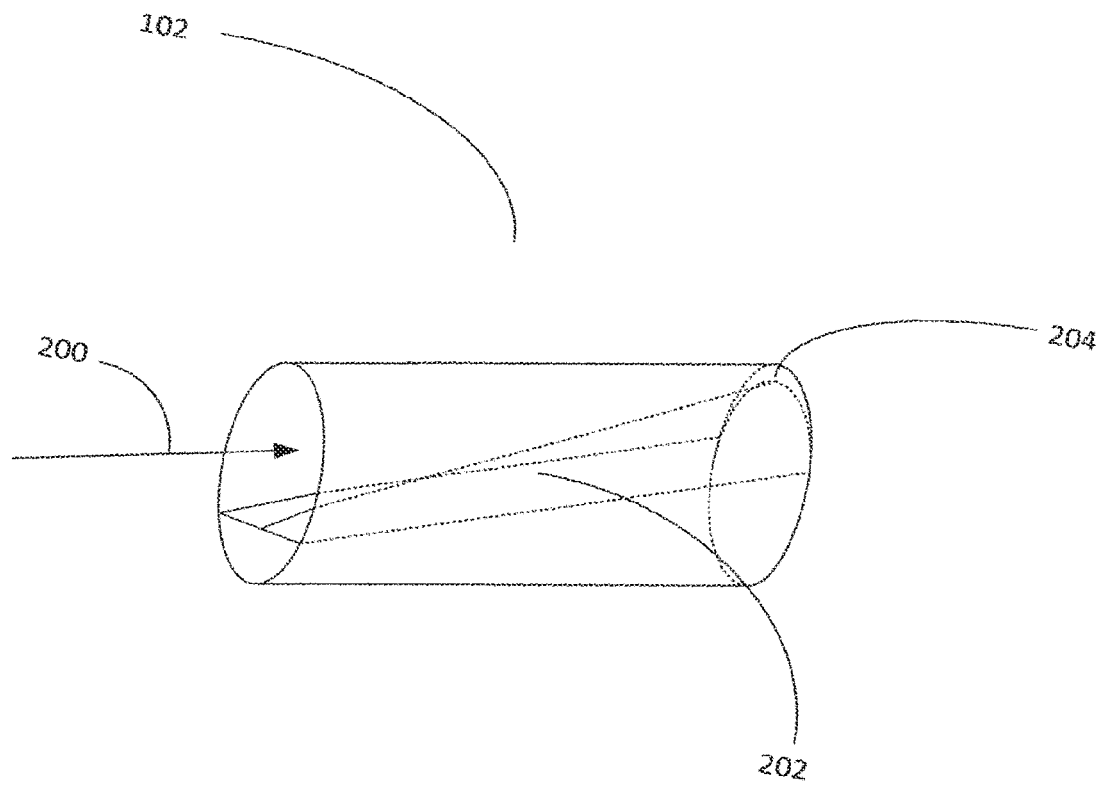
FIG. 2 illustrates a phantom view of a cylinder in accordance with an aspect of the present disclosure.

FIG. 2 illustrates a phantom view of a cylinder in accordance with an aspect of the present disclosure.

Cylinder 102 may produce a single frequency, and/or a single frequency with harmonics of the single frequency, through the flow of air and/or other gases in direction 200. As air travels in direction 200, reed 202, which may be inserted inside of cylinder 102 in one or more possible ways, oscillates and produces one or more audible tones at outlet 204.

Cylinder 102 and reed 202 may be combined in such a way to produce a specific, desired tone from device 100. Such frequencies include, but are not limited to, 136 Hertz (Hz), 396 Hz, 417 Hz, 432 Hz, 528 Hz, 639 Hz, 741 Hz, and/or 852 Hz.

Further, the airflow may be provided by the breathing of a user of device 100. By coupling the user's breath with the device 100, the user may be more closely harmonized and/or coupled with the frequency that device 100 is producing, which may have a more profound effect on the user than having the frequency generated externally, e.g., via a speaker or other external source. Although FIG. 2 illustrates airflow in direction 200, which may be produced on an exhale of a user, the airflow may be in other directions, e.g., opposite of direction 200, in addition to and/or instead of the airflow in direction 200. Such other airflows may be produced on an inhale of a user. Further, the note and/or tone produced in direction 200 may be different than the note and/or tone produced when airflow is in a direction other than direction 200 without departing from the scope of the present disclosure.

Device 100 differs from other devices, e.g., flutes, recorders, other wind instruments, etc., as these devices are used to create various notes and play in various tempos. A device in accordance with the present invention is designed, at least in part, to play a single note (with or without harmonics of the note) in a long, steady fashion. Further, the breathing exercises and lack of other muscle usage (finger movement, tongue staccato playing, etc.) that may be used to create long, steady, single-tone notes may assist in creating desired effects from device 100.

Although the present disclosure and its advantages have been described in detail, it should be understood that various changes, substitutions and alterations can be made herein without departing from the technology of the disclosure as defined by the appended claims. For example, relational terms, such as "above" and "below" may be used with respect to a device. Of course, if the device is inverted, above becomes below, and vice versa. Additionally, if oriented sideways, above and below may refer to sides of a device. Moreover, the scope of the present application is not intended to be limited to the particular configurations of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding configurations described herein may be utilized according to the present disclosure. Accordingly, the appended claims are intended to include within their scope such processes, machines, manufacture, compositions of matter, means, methods, or steps.

The description of the disclosure is provided to enable any person reasonably skilled in the art to make or use the disclosure. Various modifications to the disclosure will be readily apparent to those reasonably skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

Although several embodiments have been described in detail for purposes of illustration, various modifications may be made without departing from the scope and spirit of the present disclosure. Accordingly, the disclosure is not to be limited by the examples presented herein, but is envisioned as encompassing the scope described in the appended claims and the full range of equivalents of the appended claims.

What is claimed is:

1. A method of calming and healing a user comprising:
    wearing a device comprising two separable components wherein a first component is a cap with a cylindrical portion open at a first end and a second component is a body with a longitudinal length that has a cylindrical exterior along the entire longitudinal length and includes a passage passing through the body along the longitudinal length and wherein the passage includes a reed and wherein the exterior of the second component is sized to fit securely and removably into the first end of the first component;
    removing the second component from the first component by pulling the body out of the cap and placing a first distal end of the body to lips of the user; and
    repeatedly breathing both in and out through the body of the device oscillating the reed on both inhales and exhales by the user, wherein only a single note is created on both the inhales and the exhales regardless of an amplitude of the user's breathing;
    wherein the single note is selected from the group consisting of 136 Hertz (Hz), 396 Hz, 417 Hz, 432 Hz, 528 Hz, 639 Hz, 741 Hz, and 852 Hz.

2. The method of claim 1, wherein the single note includes at least one harmonic.

3. The method of claim 1, wherein the device is worn around a neck via a chain coupled to a ring on a top of the cap.

4. The method of claim 3, wherein the cap releasably captures the body in a manner that the body will not fall from the cap even when worn around the neck.

5. A method of calming and healing a user comprising:
    wearing a device comprising two separable components wherein a first component is a cap open at a first end and a second component is a body with a longitudinal length and includes a passage passing through the body along the longitudinal length and wherein the passage includes a reed and wherein the exterior of the second component is sized to fit securely and removably into the first end of the first component;
    removing the second component from the first component by pulling the body out of the cap and placing a first distal end of the body to lips of the user; and
    repeatedly breathing both in and out through the body of the device oscillating the reed on both inhales and exhales by the user, wherein only a single note is created on both the inhales and the exhales regardless of an amplitude of the user's breathing;

wherein the single note is selected from the group consisting of 136 Hertz (Hz), 396 Hz, 417 Hz, 432 Hz, 528 Hz, 639 Hz, 741 Hz, and 852 Hz.

6. The method of claim 5, wherein an exterior of the body is cylindrically shaped along the entire longitudinal length.

7. The method of claim 6, wherein the cap has an interior extending inward from the first end and ending in a first closed end.

8. The method of claim 5, wherein the single note includes at least one harmonic.

9. The method of claim 5, wherein the device is worn around a neck via a chain coupled to a ring on a top of the cap.

10. The method of claim 9, wherein the cap releasably captures the body in a manner that the body will not fall from the cap even when worn around the neck.

11. A method of calming and healing a user comprising:
wearing a device comprising two separable components wherein a first component is a cap open at a first end and a second component is a body with a longitudinal length and includes a passage passing through the body along the longitudinal length and wherein the passage includes a reed and wherein the exterior of the second component is sized to fit securely and removably into the first end of the first component;
removing the second component from the first component by pulling the body out of the cap and placing a first distal end of the body to lips of the user; and
repeatedly breathing both in and out through the body of the device oscillating the reed on both inhales and exhales by the user, wherein only a single note including at least one harmonic is created on both the inhales and the exhales regardless of an amplitude of the user's breathing;
wherein the single note is selected from the group consisting of 136 Hertz (Hz), 396 Hz, 417 Hz, 432 Hz, 528 Hz, 639 Hz, 741 Hz, and 852 Hz.

12. The method of claim 11, wherein an exterior of the body is cylindrically shaped along the entire longitudinal length.

13. The method of claim 12, wherein the cap has an interior extending inward from the first end and ending in a first closed end.

14. The method of claim 11, wherein the device is worn around a neck via a chain coupled to a ring on a top of the cap.

15. The method of claim 14, wherein the cap releasably captures the body in a manner that the body will not fall from the cap even when worn around the neck.

* * * * *

UNITED STATES PATENT AND TRADEMARK OFFICE
CERTIFICATE OF CORRECTION

| | | |
|---|---|---|
| PATENT NO. | : 11,986,601 B2 | |
| APPLICATION NO. | : 18/319488 | |
| DATED | : May 21, 2024 | |
| INVENTOR(S) | : Sigmar Karl Berg | |

It is certified that error appears in the above-identified patent and that said Letters Patent is hereby corrected as shown below:

On the Title Page

Item (71), Item (72), and Item (73) in the name of the Applicant/Inventor/Assignee which is currently listed as "Sigmar Paul Berg" should be corrected to "Sigmar Karl Berg".

Signed and Sealed this
Thirteenth Day of August, 2024

Katherine Kelly Vidal
*Director of the United States Patent and Trademark Office*